US007074816B2

(12) United States Patent
Nakamura et al.

(10) Patent No.: US 7,074,816 B2
(45) Date of Patent: Jul. 11, 2006

(54) 1 2 4-TRIAZOLE COMPOUND

(75) Inventors: Hiroshi Nakamura, Nagareyama (JP); Soichi Kaneda, Shiki (JP); Takahiro Sato, Kita-ku (JP); Naoki Ashizawa, Kamifukuoka (JP); Koji Matsumoto, Saitama (JP); Takashi Iwanaga, Kazo (JP); Tsutomu Inoue, Funabashi (JP)

(73) Assignee: Fuji Yakuhin Co., Ltd., Saitama (JP)

( * ) Notice: Subject to any disclaimer, the term of this patent is extended or adjusted under 35 U.S.C. 154(b) by 0 days.

(21) Appl. No.: 10/495,322

(22) PCT Filed: Dec. 3, 2002

(86) PCT No.: PCT/JP02/12662

§ 371 (c)(1),
(2), (4) Date: May 11, 2004

(87) PCT Pub. No.: WO03/064410

PCT Pub. Date: Aug. 7, 2003

(65) Prior Publication Data

US 2005/0004175 A1 Jan. 6, 2005

(30) Foreign Application Priority Data

Jan. 28, 2002 (JP) ............................. 2002-017825

(51) Int. Cl.
*C07D 249/08* (2006.01)
*A61K 31/41* (2006.01)

(52) U.S. Cl. .................................... 514/383; 548/262.2

(58) Field of Classification Search ............. 548/266.2; 546/272.4; 514/340, 383

See application file for complete search history.

(56) References Cited

U.S. PATENT DOCUMENTS 3,882,134 A * 5/1975 Baldwin et al. ............ 546/256
3,947,577 A * 3/1976 Baldwin et al. ............ 514/333
3,984,558 A * 10/1976 Baldwin et al. ............ 514/333
4,011,218 A * 3/1977 Baldwin et al. ............ 544/238
4,104,393 A * 8/1978 Baldwin et al. ............ 514/333
5,571,897 A * 11/1996 Takalo et al. ................. 534/15

OTHER PUBLICATIONS

Geldard, J.F. et al., J. Org. Chem.; 1965; 30(1); 318-319, especially p. 319, starting line 33.*
Lever, A.B.P., Inorg. Chem; 1990; 29; 1271-1285, especially p. 1275, line 18 and 19.*
Baldwin, J.J., J. Med. Chem.; 1975; 18(9); 895-900, especially p. 898, lines 3-5.*

* cited by examiner

*Primary Examiner*—Kamal A. Saeed
*Assistant Examiner*—Susannah L. Chung
(74) *Attorney, Agent, or Firm*—Price, Heneveld, Cooper, DeWitt & Litton, LLP

(57) ABSTRACT

A novel 1,2,4-triazole compound which is useful as a therapeutic agent for hyperuricemia and gout due to hyperuricemia is provided. A compound is represented by the following general formula (1):

[Chemical 6]

(1)

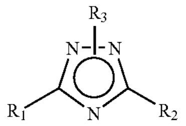

wherein $R_2$ represents an unsubstituted or substituted pyridyl group, $R_1$ represents a similar pyridyl group, a pyridine-N-oxide group corresponding to these pyridyl groups, or a phenyl group, and $R_3$ represents hydrogen or a lower alkyl group substituted with pivaloyloxy group and $R_3$ bonds to a nitrogen atom in the ring. A process for production of a compound by reacting a nitrile and a hydrazide, and a therapeutic agent, particularly a xanthine oxidase inhibitor are also provided.

8 Claims, No Drawings

1 2 4-TRIAZOLE COMPOUND

BACKGROUND OF THE INVENTION

1. Field of the Invention

The present invention relates to a novel 1,2,4-triazole compound which may be substituted at the 1, 2 or 4 position with a substituted alkyl group and has aromatic rings at the 3 and 5 positions, a hydrate or a salt thereof, a process for production thereof, and a therapeutic agent for gout and hyperuricemia comprising one of these substances as an active ingredient.

2. Description of the Related Art

The number of patients with hyperuricemia in Japan is reported to be 1.25 million and the number suffering from asymptomatic hyperuricemia is estimated to reach several millions. Hyperuricemia is becoming a popular disease.

Presently, hyperuricemia and gout due to hyperuricemia are treated by improving the living environment and administering various drug therapies for each period when an attack of gout is predicted to occur (presymptomatic period), when an attack of gout occurs, or when an attack of gout subsides. That is, preventive therapy is conducted in the presymptomatic period by administering colchicines as well as controlling the daily living environment. When an attack occurs, drug therapy using non-steroidal or steroidal anti-inflammatory agents is mainly conducted. After the attack subsides, patients are given guidance to improve their lifestyle. When improvement is judged insufficient, an assessment is made as to whether hyperuricemia is caused by reduced excretion of uric acid or by increased production of uric acid followed by treatment with drugs, which exhibit a uricosuric effect, such as probenecid and benzbromarone, those which inhibit resorption of uric acid, such as sulfinpyrazone, those which improve acidurea conditions, such as citrates, and xanthine oxidase inhibitors which inhibit production of uric acid, such as allopurinol. Colchicine is said to be able to prevent about 90% of attacks through inhibiting chemotaxis and phagocytosis of leukocytes, such as neutrophils, if administration thereof has been completed within a few hours before the attack. Since colchicine has various adverse effects, however, the use thereof is limited to the minimum and it is therefore difficult to timely administer it.

Accordingly, drug therapies are mainly adopted, but only allopurinol is available for the treatment of a disease caused by increased production of uric acid. However, a metabolite of allopurinol, oxypurinol, tends to accumulate and may cause calculi formation. Furthermore, this drug has been reported to induce adverse events such as rash, a decreased renal function and hepatitis, and it is not easy to administer.

Examples of compounds having xanthine oxidase inhibiting activity that can be used for treating gout caused by increased production of uric acid and that are effective for hyperuricemia and gout due to hyperuricemia have been described in J. Medicinal Chemistry, 1975, Vol. 18, No. 9, pp. 895–900, Japanese Patent Publication No. 49-46622 and Japanese Patent Publication No. 50-24315, which disclose some 1,3,5-substituted or 3,5-substituted 1,2,4-triazole compounds.

SUMMARY OF THE INVENTION

Hyperuricemia and gout caused by hyperuricemia tend to spread even among young people in Japan due to changes in lifestyle and the like and the diseases cannot be dealt with only by guidance aiming at improvement of lifestyle. However, compounds having improved efficacy for these diseases are difficult to obtain and development of novel therapeutic agents has made little progress by now.

An object of the present invention is to provide a novel 1,2,4-triazole compound which has a high xanthine oxidase inhibiting activity and is useful as a therapeutic agent for hyperuricemia and gout due to hyperuricemia caused by increased production of uric acid.

In short, the first aspect of the present invention relates to a 1,2,4-triazole compound represented by the following general formula (1):

[Chemical 2]

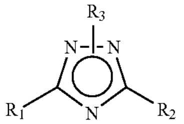

(1)

which may be substituted at the 1, 2 or 4 positions with a substituted alkyl group and has substituted aromatic rings at the 3 and 5 positions, a hydrate or a salt thereof.

The second aspect of the present invention relates to a process for the production of a 1,2,4-triazole compound represented by the above described general formula (1) in which $R_3$ is hydrogen, characterized in that the process comprises the step of reacting an iminoether of a corresponding aromatic nitrile with a hydrazide of an aromatic carboxylic acid.

The third aspect of the present invention relates to a process for the production of a 1,2,4-triazole compound represented by the above described general formula (1) in which $R_3$ is a lower alkyl group substituted with a pivaloyloxy group, characterized in that the process comprises the step of reacting a compound represented by the general formula (1) in which $R_3$ is hydrogen with a halogenated lower alkyl ester of pivalic acid.

The fourth aspect of the present invention relates to a therapeutic agent comprising a compound represented by the above described general formula (1) or a hydrate or a salt thereof as an active ingredient.

Considering only one xanthine oxidase inhibitor is commercially available, the present inventors aimed at creating a compound having an inhibitory activity against xanthine oxidase in hyperuricemia and gout due to hyperuricemia which is caused by increased production of uric acid, and continue researching focusing on 1,2,4-triazole compounds as a basic substance.

As a result, the present inventors have completed each of the above mentioned inventions.

DETAILED DESCRIPTION OF PREFERRED EMBODIMENT

Hereinafter, the present invention will be specifically described.

First of all, the groups in the above described general formula (1) will be described.

In the above described general formula, $R_2$ represents an unsubstituted pyridyl group or a substituted pyridyl group having a cyano, lower alkyl, halogen, lower alkoxy or lower alkylthio group as a substituent. $R_1$ represents an unsubstituted or substituted pyridyl group which may be substituted with a halogen, cyano or phenyl group, a pyridine-N-oxide group corresponding to these pyridyl groups, a phenyl group substituted with a cyano or nitro group or a phenyl group substituted with, in addition to a cyano or nitro group, a substituted or unsubstituted lower alkoxy group, an N-lower alkyl-piperazino group, a lower alkylthio group, a phenylthio group, or a lower alkylamino group, provided that $R_1$ is not an unsubstituted pyridyl group, a pyridyl group substituted with a lower alkyl group, or a pyridine-N-oxide group corresponding to these pyridyl groups in the case that $R_2$ is an unsubstituted pyridyl group or a pyridyl group substituted with a lower alkyl group. $R_3$ represents hydrogen or a lower alkyl group substituted with pivaloyloxy group and in each case $R_3$ bonds to one of the nitrogen atoms in the 1,2,4-triazole ring represented by the general formula (1).

In the case that both the substituents at the 3 and 5 positions of the compound of the present invention comprise pyridine rings, at least one of them is preferably substituted with a cyano group or halogen, and in the case that one of the substituents at the 3 and 5 positions is a phenyl group, the phenyl group may be substituted with a substituted or unsubstituted lower alkoxy group, thioether, a substituted piperazino group, a substituted amino group, etc., but it must be substituted with either a cyano or nitro group.

The compounds of the present invention having these combinations of substituent groups have exhibited a high xanthine oxidase inhibiting activity which had not been attained by conventional compounds in an in vivo xanthine oxidase inhibiting test, and thus the present inventors have completed the present invention.

The 1,2,4-triazole compounds as basic structure of the present invention include the following isomers (A), (B), and (C), and all of these are referred to as 1,2,4-triazole and represented by the general formula (1).

Isomer (A)

[Chemical 3]

[Chemical 3]

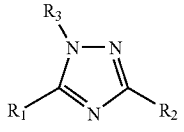

Isomer (B)

[Chemical 4]

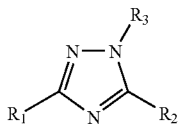

Isomer (C)

[Chemical 5]

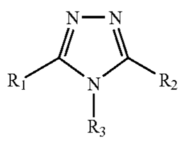

The process for the production of the compound of the present invention is based on a reaction between an iminoether of a corresponding aromatic nitrile with a hydrazide of an aromatic carboxylic acid.

That is, the process is characterized by reacting an iminoether represented by the corresponding general formula (2): $R_1CN$ with a hydrazide represented by the general formula (3): $R_2CONHNH_2$ or reacting an iminoether represented by the corresponding general formula (4): $R_2CN$ with a hydrazide represented by the general formula (5): $R_1CONHNH_2$.

Iminoethers (ethers of an imino acid) produced by reacting an aromatic nitrile with an alcohol under basic conditions wherein the alcohol may be, for example, sodium methoxide or sodium ethoxide or alternatively with an alcohol such as methanol or ethanol under acidic conditions can be used. Such salts produced under acidic conditions can be separated and iminoethers produced under basic conditions can be separated as a free compound or may be separated after converted to a salt.

Examples of the solvents usable in the production process of the present compounds include aqueous solvent such as methanol and ethanol, and methanol is preferred. The reaction can proceed at room temperature, but preferably it is conducted under heating in a viewpoint of reaction rate and elimination of water in the reaction. In the case that methanol is used as a solvent, a temperature near its boiling point (about 65° C.) is preferred, and a refluxing condition was adopted in the production examples of the present application. Reaction time can be set freely depending upon the reaction temperature as long as it falls within the range so that side reactions or production of decomposition substances may be suppressed.

In the case where a lower alkyl group substituted with a pivaloyloxy group is introduced in the compound of the present invention, the reaction can be conducted according to a conventional dehydrohalogenation reaction, and is preferably conducted in the presence of dehydrohalogenation agents such as well-known organic bases and alkalizing agents. The reaction can sufficiently proceed at room temperature and can be conducted in a solvent, an example of which includes dimethylformamide (hereinafter abbreviated as DMF).

EXAMPLES

The compounds and production processes according to the present invention and a test method for confirming the effectiveness of the compounds and results of the test will be described more specifically by way of the examples. These examples disclosed, however, should not be construed for limiting the present invention.

Dimethyl sulfoxide is hereinafter abbreviated as DMSO in the following examples.

Example 1

3-(4-isobutoxy-3-nitrophenyl)-5-(2-methyl-4-pyridyl)-1,2,4-triazole

1) Production of 4-isobutoxy-3-nitrobenzonitrile 19.5 g of 4-chloro-3-nitrobenzonitrile was dissolved in 200 ml of DMF and, after 16.0 g of 2-methyl-1-propanol, 30 g of potassium carbonate and 7.1 g of potassium iodide were added thereto, the mixture was heated and stirred at 80° C. for 24 hours. Water was added to the reaction mixture, which was then extracted with ethyl acetate. The ethyl acetate layer was washed with a saturated saline solution and dried over magnesium sulfate. After the magnesium sulfate was filtered off, solvent was evaporated under reduced pressure and the residue was subjected to silica gel column chromatography. Hexane-ethyl acetate (10:1) was used as an eluent and 5.9 g of the object compound was obtained as a pale yellow crystal. $^1$H-NMR ($CDCl_3$) δppm: 1.07 (6H, d, J=6.76 Hz), 2.11~2.25 (1H, m), 3.94 (2H, d, J=6.43 Hz), 7.15 (1H, d, J=8.91 Hz), 7.81 (1H, dd, J=8.91, 2.15 Hz), 8.14 (1H, d, J=2.15 Hz)

2) 1.54 g of the crystal obtained in 1) was dissolved in 50 ml of methanol and, after 757 mg of sodium methoxide was added thereto, the mixture was stirred at room temperature under argon atmosphere for 3 hours. 1.06 g of 2-methylisonicotinic acid hydrazide was then added and the mixture was refluxed for 16 hours. After the reaction completed, solvent was evaporated under reduced pressure and water was added to the residue, which was extracted with ethyl acetate, and dried over magnesium sulfate. After the magnesium sulfate was filtered off, the solvent was evaporated under reduced pressure. Chloroform was added to the thus obtained residue and stirred at room temperature for one hour. The precipitated solid was filtered, washed with chloroform and dried with a vacuum pump to yield 1.50 g of the object compound as a colorless powder.

$^1$H-NMR (DMSO-$d_6$) δppm: 1.01 (6H, d, J=6.60 Hz), 1.99~2.15 (1H, m), 2.57 (3H, s), 4.03 (2H, d, J=6.43 Hz), 7.56 (1H, d, J=8.91 Hz), 7.80 (1H, d, J=5.11 Hz), 7.88 (1H, s), 8.31 (1H, dd, J=8.91, 1.98 Hz), 8.54 (1H, d, J=1.98 Hz), 8.60 (1H, d, J=5.11 Hz), 14.86 (1H, s)

Example 2

3-(3-cyano-4-isobutoxyphenyl)-5-(4-pyridyl)-1,2,4-triazole

1) Production of 4-isobutoxy-3-cyanobenzonitrile 25.2 g of 4-nitrobenzonitrile was dissolved in 300 ml of DMSO, and after 20.0 g of potassium cyanide was added thereto, the mixture was heated and stirred at 100° C. for one hour. The reaction mixture was cooled to room temperature and after 81.6 g of 1-bromo-2-methylpropane and 11.76 g of potassium carbonate were added thereto, the mixture was heated and stirred at 80° C. for 8 hours. Water was added to the reaction mixture, which was then extracted with ethyl acetate. The ethyl acetate layer was washed with a saturated saline solution and dried over magnesium sulfate. After the magnesium sulfate was filtered off, the solvent was evaporated under reduced pressure and the residue was subjected to silica gel column chromatography. Hexane-ethyl acetate (3:1) was used as an eluent to yield 21.75 g of a pale yellow powder.

$^1$H-NMR ($CDCl_3$) δppm: 1.09 (6H, d, J=6.76 Hz), 2.13~2.28 (1H, m), 3.91 (2H, d, J=6.43 Hz), 7.04 (1, d, J=8.74 Hz), 7.77~7.86 (2H, m)

2) Production of the Object Compound

Sodium methoxide in a catalytic amount (0.08 g) was added to 10 ml of a methanol solution containing 0.50 g of the powder obtained in 1), and the mixture was stirred at room temperature overnight. Isonicotinic acid hydrazide was added to the reaction mixture, which was then refluxed overnight. The precipitated solid was filtered and recrystallized from methanol to yield 0.14 g of the title compound as a colorless powder.

$^1$H-NMR (DMSO-$d_6$) δppm: 1.03 (6H, d, J=6.77 Hz), 2.03~2.15 (1H, m), 4.01 (2H, d, J=6.43 Hz), 7.45 (1H, d, J=8.74 Hz), 7.99 (2H, dd, J=4.45, 1.65 Hz), 8.29~8.34 (2H, m), 8.73 (2H, dd, J=4.45, 1.65 Hz)

The following compounds were prepared according to procedures similar to those in Examples 1 and 2.

Example 3

3-[3-cyano-4-{(2-methoxy)ethoxymethyl}oxyphenyl]-5-(2-methyl-4-pyridyl)-1,2,4-triazole Pale Brown Powder $^1$H-NMR (DMSO-$d_6$) δppm: 2.57 (3H, s), 3.22 (3H, s), 3.47~3.51 (2H, m), 3.80~3.83 (2H, m), 5.52 (2H, s), 7.53 (1H, d, J=9.08 Hz), 7.79 (1H, d, J=4.95 Hz), 7.88 (1H, s), 8.30~8.35 (2H, m), 8.60 (1H, d, J=4.95 Hz)

Example 4

3-[4-(4-methyl-1-piperazino)-3-nitrophenyl]-5-(2-methyl-4-pyridyl)-1,2,4-triazole Yellow Powder $^1$H-NMR ($CDCl_3$) δppm: 2.39 (3H, s), 2.62~2.66 (7H, m), 3.19~3.23 (4H, m), 7.20 (1H, d, J=8.74 Hz), 7.81 (1H, d, J=5.11 Hz), 7.91 (1H, s), 8.15 (1H, dd, J=8.74, 1.98 Hz), 8.48 (1H, d, J=1.98 Hz), 8.63 (1H, d, J=5.11 Hz)

Example 5

3-(4-isobutylamino-3-nitrophenyl)-5-(2-methyl-4-pyridyl)-1,2,4-triazole

Orange Powder $^1$H-NMR (DMSO-$d_6$) δppm: 0.98 (6H, d, J=6.59 Hz), 1.94~2.04 (1H, m), 2.56 (1H, s), 3.17~3.32 (2H, m), 7.28 (1H, d, J=9.40 Hz), 7.77~7.87 (2H, m), 8.17 (1H, dd, J=9.40, 1.98 Hz), 8.43~8.58 (2H, m), 8.81 (1H, d, J=1.98 Hz)

Example 6

5-(2-methyl-4-pyridyl)-3-(3-nitro-4-phenylthiophenyl)-1,2,4-triazole

Yellow Powder $^1$H-NMR (DMSO-$d_6$) δppm: 2.56 (3H, s), 7.03 (1H, d, J=8.58 Hz), 7.57~7.87 (7H, m), 8.20 (1H, d, J=8.58 Hz), 8.61 (1H, d, J=5.12 Hz), 8.88 (1H, s), 15.04 (1H, s)

Example 7

3-(4-isobutylthio-3-nitrophenyl)-5-(2-methyl-4-pyridyl)-1,2,4-triazole

Yellow Powder $^1$H-NMR (DMSO-$d_6$) δppm: 1.07 (6H, d, J=6.60 Hz), 1.91~1.96 (1H, m), 2.57 (3H, s), 3.03 (2H, d, J=6.76 Hz), 7.80~7.89 (3H, m), 8.33 (1H, dd, J=8.41, 1.98 Hz), 8.61 (1H, d, J=5.12 Hz), 8.84 (1H, d, J=1.98 Hz)

Example 8

5-(2-methyl-4-pyridyl)-3-(3-nitro-4-phenylthiomethyloxyphenyl)-1,2,4-triazole

Pale Yellow Powder $^1$H-NMR (DMSO-$d_6$) δppm: 2.57 (3H, s), 5.95 (2H, s), 7.27~7.51 (5H, m), 7.71~7.88 (3H, m), 8.33 (1H, dd, J=8.91, 2.15 Hz), 8.53~8.61 (2H, m), 14.92 (1H, s)

Example 9

5-(2-methyl-4-pyridyl)-3-(4-methylthiomethyloxy-3-nitrophenyl)-1,2,4-triazole

Yellow Powder $^1$H-NMR (DMSO-$d_6$) δppm: 2.22 (3H, s), 2.57 (3H, s), 5.58 (2H, s), 7.65~7.89 (3H, m), 8.31 (1H, dd, J=8.41, 1.65 Hz), 8.54~8.61 (2H, m), 14.94 (1H, s)

Example 10

3-(4-benzyloxymethyloxy-3-nitrophenyl)-5-(2-methyl-4-pyridyl)-1,2,4-triazole

Pale Yellow Powder $^1$H-NMR ($CDCl_3$) δppm: 2.68 (3H, s), 4.79 (2H, s), 5.48 (2H, s), 7.30~7.38 (5H, m), 7.52 (1H, d, J=8.90 Hz), 7.79 (1H, d, J=5.44 Hz), 7.90 (1H, s), 8.24 (1H, dd, J=8.90, 2.14 Hz), 8.57 (1H, d, J=2.14 Hz), 8.66 (1H, d, J=5.44 Hz)

Example 11

5-(2-methyl-4-pyridyl)-3-[3-nitro-4-(2-tetrahydropyranylmethyl)oxyphenyl]-1,2,4-triazole Pale Yellow Powder $^1$H-NMR (DMSO-$d_6$) δppm: 1.35~1.81 (6H, m), 2.57 (3H, s), 3.43~4.26 (4H, m), 7.58 (1H, d, J=8.91 Hz), 7.80 (1H, d, J=4.62 Hz), 7.88 (1H, s), 8.30 (1H, dd, J=8.91, 1.82), 8.53 (1H, d, J=1.82 Hz), 8.60 (1H, d, J=4.62 Hz)

Example 12

5-(2-cyano-4-pyridyl)-3-(4-pyridyl)-1,2,4-triazole

1) Production of methyl isonicotinate N-oxide 13.9 g of isonicotinic acid N-oxide was added to 209 ml of methylene chloride, 29.7 g of 1-ethoxycarbonyl-2-ethoxy-1,2-dihydroquinoline was further added thereto, and the mixture was stirred under argon atmosphere at room temperature for one hour. 32.1 g of methanol was added to this mixture, which was stirred at room temperature for 17 hours. After the solvent was evaporated under reduced pressure, the residue was subjected to silica gel column chromatography. Chloroform-acetone (3:1) was used as an eluent to yield 11.1 g of a white powder.

$^1$H-NMR ($CDCl_3$) δppm: 3.95 (3H, s), 7.88 (2H, d, J=7.25 Hz), 8.22 (2H, J=7.25 Hz)

2) Production of Methyl 2-cyanoisonicotinate 11.1 g of the crystal obtained in 1) was dissolved in 170 ml of acetonitrile, 14.6 g of triethylamine and 21.5 g of trimethylsilylnitrile were added thereto, and the mixture was refluxed under argon atmosphere for 16 hours. After the solvent was evaporated under reduced pressure, the residue was subjected to silica gel column chromatography. Chloroform-acetone (95:5) was used as an eluent to yield 8.44 g of a pale yellow powder.

$^1$H-NMR ($CDCl_3$) δppm: 4.01 (3H, s), 8.08 (1H, d, J=5.45 Hz), 8.24 (1H, s), 8.90 (1H, d, J=5.45 Hz)

3) Production of 2-cyanoisonicotinic acid hydrazide 8.44 g of the crystal obtained in 2) was added to 85 ml of methanol, 1.84 g of hydrazine was further added thereto, and the mixture was stirred under argon temperature for 2 hours. After the solvent was evaporated under reduced pressure, chloroform was added to the residue, which was stirred at room temperature for one hour. The precipitated crystal was filtered, washed with chloroform and dried with a vacuum pump to yield 4.15 g of a pale yellow powder.

$^1$H-NMR (DMSO-$d_6$) δppm: 4.72 (2H, s), 8.05 (1H, d, J=5.12 Hz), 8.31 (1H, s),8.90 (1H, d, J=5.12 Hz), 10.23 (1H, s)

4) Production of the Object Compound 2.67 g of 4-cyanopyridine was dissolved in 40 ml of methanol, 0.83 g of sodium methoxide was added thereto, and the mixture was stirred at room temperature for one hour. Then 4.15 g of the crystal obtained in 3) was added and the mixture was refluxed for 37 hours. After the reaction completed, the precipitated solid was filtered, washed with methanol and dried with a vacuum pump to yield 3.66 g of the object compound as a yellow powder.

$^1$H-NMR (DMSO-$d_6$) δppm: 8.01 (2H, dd, J=4.54, 1.57 Hz), 8.31 (1H, dd, J=5.11, 1.65 Hz), 8.53 (1H, dd, J=1.65, 0.50 Hz), 8.80 (2H, dd, J=4.54, 1.57 Hz), 8.93 (1H, dd, J=5.11, 0.50 Hz)

Example 13

3-(4-isobutoxy-3-nitrophenyl)-5-(4-pyridyl)-1,2,4-triazole

A white powder was obtained according to procedures similar to those in Example 1.

$^1$H-NMR (DMSO-$d_6$) δppm: 1.01 (6H, d, J=6.60 Hz), 2.00~2.12 (1H, m), 4.04 (2H, d, J=6.43 Hz), 7.57 (1H, d, J=9.07 Hz), 8.00 (2H, d, J=6.10 Hz), 8.31 (1H, dd, J=6.10, 1.98 Hz), 8.55 (1H, d, J=1.98 Hz), 8.74 (2H, d, J=6.10 Hz), 14.92 (1H, s)

Example 14

3-(4-isobutoxy-3-nitrophenyl)-5-(2-methyl-4-pyridyl)-N-pivaloyloxymethyl-1,2,4-triazole 354 mg of the powder obtained in Example 1 was dissolved in 3 ml of DMF, 181 mg of pivaloyloxymethyl chloride and 276 mg of potassium carbonate were added thereto, and the mixture was stirred at room temperature for 18 hours. Ethyl acetate was added to the reaction mixture, which was then washed with water and dried over magnesium sulfate. After the magnesium sulfate was filtered off, the solvent was evaporated under reduced pressure and the residue was subjected to silica gel column chromatography. Chloroform-acetone (95:5) was used as an eluent and 358 mg of the object compound was obtained as a white powder.

$^1$H-NMR ($CDCl_3$) δppm: 1.06~1.11 (6H, m), 1.26~1.27 (9H, m), 2.11~2.29 (1H, m), 2.64~2.68 (3H, m), 3.91~3.98 (2H, m), 6.13~6.19 (2H, m), 7.12~7.26 (2H, m), 7.49~7.59 (2H, m), 7.82~8.05 (3H, m), 8.27~8.37 (2H, m), 8.60~8.72 (3H, m)

The following compounds were prepared according to procedures similar to those in Examples 1, 2 or 12.

Example 15

3-(4-butoxy-3-nitrophenyl)-5-(4-pyridyl)-1,2,4-triazole

Pale Green Crystal $^1$H-NMR (DMSO-$d_6$) δppm: 1.34 (3H, t, J=7.29 Hz), 1.70 (2H, m), 1.75 (2 H, m), 7.60 (1H, d, J=8.91 Hz), 8.00 (each 2H, d, J=5.94 Hz), 8.29 (1H, dd, J=8.91, 2.16 Hz), 8.50 (1H, d, J=2.16 Hz), 8.74 (each 2H, d, J=5.94 Hz)

Example 16

5-(4-isopropoxy-3-nitrophenyl)-3-(4-pyridyl)-1,2,4-triazole

Pale Yellow Crystal $^1$H-NMR (DMSO-$d_6$) δppm: 1.34 (3H, d, J=5.94 Hz), 1.36 (3H, d, J=5.94 Hz), 4.94 (1H, m), 7.60 (1H, d, J=8.91 Hz), 8.00 (each 2H, d, J=5.94 Hz), 8.29 (1H, dd, J=8.91, 2.16 Hz), 8.50 (1H, d, J=2.16 Hz), 8.74 (each 2H, d, J=5.94 Hz)

Example 17

5-(2-chloro-4-pyridyl)-3-(4-isobutoxy-3-nitrophenyl)-1,2,4-triazole

Brown Crystal $^1$H-NMR (DMSO-$d_6$) δppm: 0.97 (3H, d, J=6.48 Hz), 1.01 (3H, d, J=6.48 Hz), 2.08 (1H, m), 4.04 (2H, d, J=6.48 Hz), 7.58 (1H, d, J=9.18 Hz), 8.01~8.05 (2H, m), 8.31 (1H, dd, J=9.18, 2.16 Hz), 8.56~8.58 (2H, m)

Example 18

3-(2-pyridyl)-5-(3-nitro-4-isobutoxyphenyl)-1,2,4-triazole

Pale Yellow Powder $^1$H-NMR (DMSO-$d_6$) δppm: 1.01 (6H, d, J=6.76 Hz), 2.08 (1H, m), 4.02 (2H, d, J=6.43 Hz), 7.54 (2H, m), 8.03 (1H, t, J=7.67 Hz), 8.19 (1H, d, J=7.92 Hz), 8.31 (1H, d, J=8.91 Hz), 8.50 (1H, s), 8.74 (1H, d, J=4.62 Hz), 14.93 (1H, brs)

Example 19

3-(3-pyridyl)-5-(3-nitro-4-isobutoxyphenyl)-1,2,4-triazole

Grayish White Powder $^1$H-NMR (DMSO-$d_6$) δppm: 1.01 (6H, d, J=6.60 Hz), 2.08 (1H, m), 4.03 (2H, d, J=6.27 Hz), 7.57 (2H, m), 8.32 (1H, dd, J=1.98, 8.91 Hz), 8.41 (1H, d, J=8.08 Hz), 8.54 (1H, d, J=1.98 Hz), 8.68 (1H, d, J=3.79 Hz), 9.25 (1H, d, J=2.15 Hz)

Example 20

3-(2-methyl-4-pyridyl)-5-(3-cyano-4-isobutoxyphenyl)-1,2,4-triazole

White Powder $^1$H-NMR (DMSO-$d_6$) δppm: 1.04 (6H, d, J=6.76 Hz), 2.11 (1H, m), 2.57 (3 H, s), 4.01 (2H, d, J=6.60 Hz), 7.45 (1H, d, J=8.58 Hz) 7.79 (1H, d, J=5.11 Hz), 7.88 (1H, s), 8.30 (1H, d, J=8.74 Hz), 8.33 (1H, s), 8.59 (1H, d, J=5.11 Hz)

Example 21

3-(2-methyl-4-pyridyl)-5-(3-nitro-4-methoxyphenyl)-1,2,4-triazole

Yellowish White Powder $^1$H-NMR (DMSO-$d_6$) δppm: 2.57 (3H, s), 4.02 (3H, s), 7.58 (1H, d, J=9.07 Hz), 7.80 (1H, d, J=5.11 Hz), 7.88 (1H, s), 8.34 (1H, dd, J=2.31, 8.91 Hz), 8.55 (1 H, d, J=2.31 Hz), 8.60 (1H, d, J=5.11 Hz)

Example 22

3-(2-methyl-4-pyridyl)-5-(3-cyano-4-cyclopropylmethoxyphenyl)-1,2,4-triazole

Pale Brown Powder $^1$H-NMR (DMSO-$d_6$) δppm: 0.42 (2H, m), 0.65 (2H, m), 1.31 (1H, m), 2.57 (3H, s), 4.10 (2H, d, J=7.09 Hz), 7.44 (1H, d, J=8.60 Hz), 7.79 (1H, d, J=5.11 Hz), 7.88 (1H, s), 8.31 (1H, d, J=9.07 Hz), 8.33 (1H, s), 8.59 (1H, d, J=5.11 Hz)

Example 23

3-(2-cyano-4-pyridyl)-5-(2-methyl-4-pyridyl)-1,2,4-triazole

Pale Yellow Powder $^1$H-NMR (DMSO-$d_6$) δppm: 7.81 (1H, d, J=5.61 Hz), 7.90 (1H, s), 8.31 (1H, dd, J=0.99, 5.11 Hz), 8.54 (1H, s), 8.66 (1H, d, H=5.11 Hz), 8.92 (1H, d, H=5.11 Hz)

Example 24

3-(2-methyl-4-pyridyl)-5-[3-cyano-4-(4-methoxybenzyloxy)phenyl]-1,2,4-triazole

White Powder $^1$H-NMR (DMSO-$d_6$) δppm: 2.57 (3H, s), 3.78 (3H, s), 5.29 (2H, s), 7.00 (2H, d, J=8.74 Hz), 7.46 (2H, d, J=8.74 Hz), 7.57 (1H, d, J=8.74 Hz), 7.79 (1H, d, J=4.78 Hz), 7.88 (1H, s), 8.33 (1H, dd, J=2.15, 8.74 Hz), 8.34 (1H, s), 8.59 (1H, d, 5.11 Hz)

Example 25

3-(2-methyl-4-pyridyl)-5-(3-cyano-4-isopentyloxyphenyl)-1,2,4-triazole

White Powder $^1$H-NMR (DMSO-$d_6$) δppm: 0.97 (6H, d, J=6.60 Hz), 1.70 (2H, m), 1.84 (1H, m), 2.57 (3H, s), 4.26 (2H, t, J=6.52 Hz), 7.48 (1H, d, J=8.58 Hz), 7.79 (1H, d, J=4.78 Hz), 7.88 (1H, s), 8.32 (1H, dd, J=2.31, 8.58 Hz), 8.33 (1H, s), 8.59 (1H, d, J=4.78 Hz), 14.80 (1H, brs)

Example 26

3-(2-methyl-4-pyridyl)-5-(3-cyano-4-methoxyphenyl)-1,2,4-triazole

Brown Powder $^1$H-NMR (DMSO-$d_6$) δppm: 2.57 (3H, s), 4.01 (3H, s), 7.47 (1H, d, J=5.77 Hz), 7.88 (1H, s), 8.35 (2H, m), 8.59 (1H, d, J=5.28 Hz)

Example 27

3-(2-chloro-4-pyridyl)-5-(2-methyl-4-pyridyl)-1,2,4-triazole

Pale Brown Powder $^1$H-NMR (DMSO-$d_6$) δ ppm: 7.80 (1H, d, J=5.28 Hz), 7.89 (1H, s), 8.02 (1H, d, J=5.11 Hz), 8.05 (1H, s), 8.59 (1H, d, J=5.11 Hz), 8.64 (1H, d, J=5.11 Hz)

Example 28

3-(2-methyl-4-pyridyl)-5-(3-cyano-4-propargyloxyphenyl)-1,2,4-triazole

Pale Brown Powder $^1$H-NMR (DMSO-$d_6$) δppm: 2.57 (3H, s), 3.76 (1H, s), 5.12 (2H, d, J=1.81 Hz), 7.52 (1H, d, J=8.41 Hz), 7.79 (1H, d, J=5.61), 7.88 (1H, s), 8.36 (1H, d, J=8.25 Hz), 8.37 (1H, s), 8.60 (1H, d, J=5.11 Hz)

Example 29

3-(2-methyl-4-pyridyl)-5-[3-cyano-4-{(<2-chloroethoxy>ethoxy)ethoxy}phenyl]-1,2,4-triazole White Powder $^1$H-NMR (DMSO-$d_6$) δppm: 2.79 (3H, s), 3.59~3.72 (8H, m), 3.85 (2H, m), 4.40 (2H, m), 7.53 (1H, d, J=8.91 Hz), 8.31 (1H, d, J=5.28 Hz), 8.38 (1H, dd, J=1.98, 8.91 Hz), 8.43 (2H, brs), 8.83 (1H, d, J=6.10 Hz)

Example 30

3-(2-isobutylthio-4-pyridyl)-5-(3-nitro-4-isobutoxyphenyl)-1,2,4-triazole

Yellow Powder $^1$H-NMR ($CDCl_3$) δppm: 1.06 (6H, d, J=6.60 Hz), 1.08 (6H, d, J=5.61 Hz), 1.99 (1H, m), 2.19 (1H, m), 3.14 (2H, d, J=6.76 Hz), 3.94 (2H, d, J=6.43 Hz), 7.17 (1H, d, J=8.91 Hz), 7.60 (1H, d, J=4.45 Hz), 7.85 (1H, s), 8.22 (1H, dd, J=1.98, 8.74 Hz), 8.53 (1H, s), 8.54 (1H, d, J=5.11 Hz)

Example 31

3-(2-methyl-4-pyridyl)-5-(3-cyano-4-methoxyethoxyphenyl)-1,2,4-triazole

White Powder $^1$H-NMR ($CDCl_3$) δppm: 2.65 (3H, s), 3.51 (3H, s), 3.87 (2H, t, J=4.70 Hz), 4.33 (2H, t, J=4.62 Hz), 7.16 (1H, d, J=8.58 Hz), 7.82 (1H, brs), 7.91 (1H, s), 8.28 (1H, dd, J=2.15, 8.58 Hz), 8.31 (1H, s), 8.56 (1H, d, J=5.28 Hz)

Example 32

3-(2-methyl-4-pyridyl)-5-[3-cyano-4-{(2-methoxyethoxy)ethoxy}phenyl]-1,2,4-triazole White Powder $^1$H-NMR ($CDCl_3$) δppm: 2.66 (3H, s), 3.42 (3H, s), 3.66 (2H, m), 3.84 (2H, m), 3.96 (2H, m), 4.25 (2H, m), 7.01 (1H, d, J=8.91 Hz), 7.78 (1H, d, J=5.28 Hz), 7.89 (1H, s), 8.19 (1H, dd, J=2.31, 8.74 Hz), 8.26 (1H, d, J=2.14 Hz), 8.63 (1H, d, J=5.11 Hz)

Example 33

3-(2-methyl-4-pyridyl)-5-[3-cyano-4-{(<2-methoxyethoxy>ethoxy)ethoxy}phenyl]-1,2,4-triazole White Powder $^1$H-NMR (DMSO-$d_6$) δppm: 2.81 (3H, s), 3.23 (3H, s), 3.43 (2H, m), 3.51~3.57 (4H, m), 3.65 (2H, m), 3.84 (2H, m), 4.39 (2H, m), 7.53 (1H, d, J=8.91 Hz), 8.33 (1H, d, J=6.02 Hz), 8.39 (1H, d, J=8.91 Hz), 8.44 (2H, s), 8.84 (1H, d, J=6.02 Hz)

Example 34

3-(2-methoxy-4-pyridyl)-5-(3-nitro-4-isobutoxyphenyl)-1,2,4-triazole

Yellow Crystal $^1$H-NMR (DMSO-$d_6$) δppm: 1.01 (6H, d, J=6.76 Hz), 2.08 (1H, m), 3.92 (3H, s), 4.03 (2H, d, J=6.43 Hz), 7.40 (1H, s), 7.55 (1H, d, J=8.74 Hz), 7.61 (1H, d, J=5.77 Hz), 8.30 (1H, dd, J=2.15, 8.75 Hz), 8.32 (1H, d, J=5.11 Hz), 8.53 (1H, d, J=1.98 Hz), 14.88 (1H, brs)

Example 35

3-(2-cyano-4-pyridyl)-5-(1-oxy-4-pyridyl)-1,2,4-triazole

Yellow Powder $^1$H-NMR (DMSO-$d_6$) δppm: 8.01 (2H, dd, J=1.98, 5.36 Hz), 8.29 (1H, dd, J=1.65, 5.11 Hz), 8.40 (2H, dd, J=1.98, 5.36 Hz), 8.52 (1H, d, J=1.65 Hz), 8.92 (1H, dd, J=1.65, 5.11 Hz)

Example 36

3-(2-cyano-4-pyridyl)-5-[3-cyano-4-{(2-methoxyethoxy)ethoxy}phenyl]-1,2,4-triazole Pale Yellow Powder $^1$H-NMR ($CDCl_3$) δppm: 3.41 (3H, s), 3.60 (2H, m), 3.79 (2H, m), 3.97 (2H, m), 4.35 (2H, m), 7.18 (1H, d, J=7.24 Hz), 8.24~8.28 (3H, m), 8.45 (1H, s), 8.81 (1H, d, J=5.28 Hz)

Example 37

3-(2-cyano-4-pyridyl)-5-(2-chloro-4-pyridyl)-1,2,4-triazole

Pale Yellow Powder $^1$H-NMR (DMSO-$d_6$) δppm: 8.02 (1H, d, J=5.11 Hz), 8.08 (1H, s), 8.31 (1H, dd, J=1.65, 5.11 Hz), 8.55 (1H, s), 8.63 (1H, d, J=5.11 Hz), 8.94 (1H, d, J=5.11 Hz)

Example 38

3-(2-cyano-4-pyridyl)-5-(2-phenyl-4-pyridyl)-1,2,4-triazole

Pale Yellow Powder $^1$H-NMR (DMSO-$d_6$) δppm: 7.55 (3H, m), 7.98 (1H, d, J=4.95 Hz), 8.17 (2H, m), 8.35 (1H, d, J=4.95 Hz), 8.58 (2H, m), 8.88 (2H, d, J=4.95 Hz), 8.93 (1H, d, J=4.95 Hz)

Example 39

5-(2-cyano-4-pyridyl)-3-(4-pyridyl)-1,2,4-triazole

1) Production of isonicotinic acid (N-2-tert-butoxycarbonyl)hydrazide-1-oxide 585 ml of methylene chloride was added to 39.0 g of isonicotinic acid N-oxide, and after 34.0 g of triethylamine was further added thereto, the mixture was cooled under argon atmosphere to −15° C. 33.5 g of ethyl chlorocarbonate in 117 ml of methylene chloride was added dropwise to this mixture, which was stirred at a temperature from −5 to −10° C. for one hour. Then 44.4 g of tert-butyl ester of carbamic acid in 117 ml of methylene chloride was added dropwise to this mixture and it was allowed to slowly rise to room temperature while it was stirred. The precipitated solid was filtered after 15 hours, washed with methylene chloride, and dried with a vacuum pump to yield 49.7 g of white crystal.

$^{1}$H-NMR (DMSO-$d_6$) δppm: 1.42 (9H, s), 7.82 (2H, d, J=7.09 Hz), 8.33 (2H, d, J=7.09 Hz), 9.02 (1H, s), 10.44 (1H, s)

Production of 2-cyanoisonicotinic acid hydrazine 1½ P-Toluenesulfonic acid salt 228 ml of dioxane was added to 30.4 g of the crystal obtained in 1), and after 13.1 g of trimethylsilyl cyanide and 38.8 g of N,N-dimethylcarbamoyl chloride were further added thereto, the mixture was stirred under argon atmosphere at 60° C. for 5 hours. After the solvent was evaporated under reduced pressure, the residue was dissolved in ethyl acetate and subsequently washed with 1.5 M sodium carbonate aqueous solution and a saturated saline solution and dried over magnesium sulfate. After the magnesium sulfate was filtered off, the solvent was evaporated under reduced pressure. Ethyl acetate was added to the residue, 68.5 g of p-toluenesulfonic acid monohydrate was added thereto, and the mixture was stirred at room temperature for 22 hours. The precipitated crystal was filtered, washed with ethyl acetate, and dried with a vacuum pump to yield 40.3 g of white crystal 2).

$^{1}$H-NMR (DMSO-$d_6$) δppm: 2.28 (4.5H, s), 7.12 (3H, dd, J=7.92 & 0.66 Hz), 7.48 (3H, dd, J=7.92 & 0.66 Hz), 8.10 (1H, dd, J=5.11 & 1.81 Hz), 8.39 (1H, dd, J=1.81 & 0.33 Hz), 8.99 (1H, dd, J=5.11 & 0.33 Hz)

3) Production of 5-(2-cyano-4-pyridyl)-3-(4-pyridyl)-1,2,4-triazole 9.98 g of 4-cyanopyridine was dissolved in 250 ml of methanol, and after 7.77 g of sodium methoxide was added thereto, the mixture was stirred at room temperature for one hour. Then 40.3 g of the crystal obtained in 2) was added and the mixture was refluxed for 24 hours. After the reaction completed, the precipitated crystal was filtered, washed with methanol, and dried with a vacuum pump to yield 16.3 g of yellow crystal.

$^{1}$H-NMR (DMSO-$d_6$) δppm: 8.01 (2H, dd, J=4.54 & 1.57 Hz), 8.31 (1H, dd, J=5.11 & 1.65 Hz), 8.53 (1H, dd, J=1.65 & 0.50 Hz), 8.80 (2H, dd, J=4.54 & 1.57 Hz), 8.93 (1H, dd, J=5.11 & 0.50 Hz)

4) Production of 5-(2-cyano-4-pyridyl)-3-(4-pyridyl)-1,2,4-triazole 45 ml of ethanol and 15 ml of 1-methyl-2-pyrrolidone were added to 3.0 g of the crystal obtained in 3), and the mixture was heated and stirred at 80° C. for 19 hours. The crystal was filtered, subsequently washed with a mixture of ethanol and 1-methyl-2-pyrrolidone (3:1) and ethanol, and dried with a vacuum pump to yield 2.71 g of yellow crystal.

5) Production of 5-(2-cyano-4-pyridyl)-3-(4-pyridyl)-1,2,4-triazole p-toluenesulfonic acid salt 5 ml of ethanol and 30 ml of water were added to 2.48 g of the crystal obtained in 4), and after 3.8 g of p-toluenesulfonic acid monohydrate was further added thereto, the mixture was stirred at room temperature for 5 hours. The precipitated crystal was filtered, subsequently washed with a mixture of ethanol and water (1:6), water and then ethanol, and dried with a vacuum pump to yield 3.5 g of white crystal.

$^{1}$H-NMR (DMSO-$d_6$) δppm: 2.28 (3H, s), 7.12 (2H, dd, J=7.75 & 0.50 Hz), 7.48 (2H, dd, J=7.75 & 0.50 Hz), 8.33 (1H, dd, J=5.12 & 1.65 Hz), 8.45 (2H, d, J=6.11 Hz), 8.57 (1H, dd, J=1.65 & 0.66 Hz), 8.96~9.02 (3H, m)

6) Production of the object compound 17 ml of ethanol and 17 ml of water were added to 3.36 g of the crystal obtained in 5), and the mixture was stirred at room temperature for 30 minutes. A solution of sodium carbonate (0.74 g of sodium carbonate in 17 ml of water) was further added, and the mixture was stirred at room temperature for 2 hours. The precipitated crystal was filtered, subsequently washed with water and ethanol, and dried with a vacuum pump to yield 1.89 g of the object compound as a pale yellow crystal.

TEST EXAMPLES

Method for Evaluating the Effect of Lowering Serum Uric Acid Level In Vivo

Each of the test compounds was suspended in a 0.5% methylcellulose (MC) aqueous solution and administered orally to seven-week-old male Wistar rats (4 rats per group) compulsorily through a feeding tube at a dose of 0.3 mg/5 ml/kg (1 mg/5 ml/kg for Example 17 and Compound 44 of J. Medicinal Chemistry, (1975) as a control). The blood was collected from the orbital sinus at 6 hours after administration of the test compound. Each blood sample was allowed to clot for one hour and then centrifuged at 2000×g for 10 minutes to obtain serum. The uric acid level in the serum was determined using a kit (Wako Pure Chemicals Industries, Ltd.; phosphotungstic acid method) and a reduction rate of serum uric acid level was calculated by the following formula:

Reduction rate of serum uric acid level=(1-Average serum uric acid level in the group receiving a test compound/Average serum uric acid level in the group receiving MC)×100

TABLE 1

| | Reduction rate of serum uric acid level |
|---|---|
| Example 1 | 66.5% |
| Example 2 | 62.3% |
| Example 3 | 40.0% |
| Example 4 | 43.9% |
| Example 5 | 39.9% |
| Example 6 | 40.6% |
| Example 7 | 42.7% |
| Example 8 | 32.5% |
| Example 9 | 35.7% |
| Example 10 | 41.6% |
| Example 11 | 41.6% |
| Example 12 | 51.1% |
| Example 13 | 46.8% |
| Example 14 | 43.0% |
| Example 15 | 41.2% |
| Example 16 | 36.1% |

TABLE 2

| | Reduction rate of serum uric acid level |
|---|---|
| Example 17 | 40.6% |
| Example 20 | 67.5% |
| Example 21 | 52.9% |
| Example 22 | 32.6% |
| Example 23 | 41.1% |
| Example 24 | 38.3% |
| Example 25 | 47.2% |
| Example 26 | 37.9% |
| Example 27 | 32.9% |
| Example 28 | 35.3% |
| Example 29 | 40.7% |
| Example 31 | 36.5% |
| Example 32 | 52.0% |
| Example 33 | 44.7% |
| Example 35 | 46.8% |
| Example 37 | 33.6% |

Positive Control

Japanese Patent Publication No. 49-46622 (Compound of Example 3) −11.1%

Japanese Patent Publication No. 50-24315 (Compound of Example 2) 26.1%

Japanese Patent Publication No. 50-24315 (Compound of Example 1) −0.4%

J. Medicinal Chemistry, 1975, Vol. 18, No. 9 (Compound 44) −7.7%

1,2,4-triazole compounds which have a high xanthine oxidase inhibiting activity and are useful as therapeutic agents for hyperuricemia and gout due to hyperuricemia caused by increased production of uric acid have been provided by selecting the compounds represented by the general formula (1) according to the present invention.

The invention claimed is:

1. A 1,2,4-triazole compound represented by the following general formula (1):

[Chemical 1]

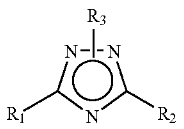

(1)

wherein $R_2$ represents an unsubstituted pyridyl group or a pyridyl group substituted with a cyano, lower alkyl, halogen, lower alkoxy or lower alkylthio group as a substituent, $R_1$ represents an unsubstituted or substituted pyridyl group which may be substituted with a halogen, cyano or phenyl group as a substituent, a pyridine-N-oxide group corresponding to these pyridyl groups, a phenyl group substituted with a cyano or nitro group or a phenyl group substituted with, in addition to a cyano or nitro group as a substituent, a substituted or unsubstituted lower alkoxy group, an N-lower alkyl-piperazino group, a lower alkylthio group, a phenylthio group, or a lower alkylamino group, provided that $R_1$ is not either a phenyl group substituted with only one cyano group or a phenyl group substituted with only one nitro group and provided that $R_1$ is not an unsubstituted pyridyl group, a pyridyl group substituted with a lower alkyl group or a pyridine-N-oxide group corresponding to these pyridyl groups in the case that $R_2$ is an unsubstituted pyridyl group, or a pyridyl group substituted with a lower alkyl group, and $R_3$ represents hydrogen or a lower alkyl group substituted with pivaloyloxy group and in each case $R_3$ bonds to one of the nitrogen atoms in the 1,2,4-triazole ring represented by the general formula (1), or a hydrate or a salt thereof.

2. The compound according to claim 1, wherein $R_1$ is a substituted phenyl group having a cyano or nitro group and a substituted or unsubstituted lower alkoxy group as substituents, or a hydrate or a salt thereof.

3. The compound according to claim 1, wherein $R_2$ is a substituted pyridyl group having a cyano or lower alkyl group as a substituent, or a hydrate or a salt thereof.

4. A drug comprising a compound according to claim 1 or a hydrate or a salt thereof as an active ingredient.

5. The drug according to claim 2 which functions as an anti-gout agent.

6. The drug according to claim 2 which functions as an anti-hyperuricemic agent.

7. A process for production of a 1,2,4-triazole compound represented by the general formula (1) according to claim 1 in which $R_3$ is hydrogen, wherein the process comprises the step of reacting an iminoether of a corresponding aromatic nitrile with a hydrazide of an aromatic carboxylic acid.

8. A process for production of a 1,2,4-triazole compound represented by the general formula (1) according to claim 1 in which $R_3$ is a lower alkyl group substituted with pivaloyloxy group, wherein the process comprises the step of reacting a compound represented by the general formula (1) in which $R_3$ is hydrogen with a halogenated lower alkyl ester of pivalic acid.

* * * * *

UNITED STATES PATENT AND TRADEMARK OFFICE

CERTIFICATE OF CORRECTION

PATENT NO. : 7,074,816 B2

APPLICATION NO. : 10/495322

DATED : July 11, 2006

INVENTOR(S) : Hiroshi Nakamura et al.

It is certified that error appears in the above-identified patent and that said Letters Patent is hereby corrected as shown below:

Column 13:

Line 4, Before “Production” insert --2)--.

Line 5, Delete “P-Toluenesulfonic” and insert --p-toluenesulfonic--.

Signed and Sealed this

Sixth Day of March, 2007

JON W. DUDAS

*Director of the United States Patent and Trademark Office*